US007569733B2

(12) United States Patent
Brocke et al.

(10) Patent No.: US 7,569,733 B2
(45) Date of Patent: Aug. 4, 2009

(54) 6-METHYL-4-(2',2',3'-TRIMETHYL-3'-CYCLOPENTEN-1'-YL)-2-CYCLOHEXEN-1-OL AS SANDAL ODORIFEROUS SUBSTANCE

(75) Inventors: Constanze Brocke, Mainz (DE); Marcus Eh, Holzminden (DE); Egon Oelkers, Bevern (DE)

(73) Assignee: Symrise GmbH & Co. KG, Holzminden (DE)

( * ) Notice: Subject to any disclaimer, the term of this patent is extended or adjusted under 35 U.S.C. 154(b) by 0 days.

(21) Appl. No.: 12/209,565

(22) Filed: Sep. 12, 2008

(65) Prior Publication Data

US 2009/0081140 A1 Mar. 26, 2009

(30) Foreign Application Priority Data

Sep. 20, 2007 (EP) .................................. 07116875

(51) Int. Cl.
*C07C 49/603* (2006.01)
*C07C 35/18* (2006.01)
*A61K 8/18* (2006.01)

(52) U.S. Cl. .......................... 568/377; 568/379; 512/23

(58) Field of Classification Search ....................... None
See application file for complete search history.

(56) References Cited

U.S. PATENT DOCUMENTS 5,189,013 A 2/1993 Chapuis et al.

*Primary Examiner*—Sikarl A Witherspoon
(74) *Attorney, Agent, or Firm*—Connolly Bove Lodge & Hutz LLP

(57) ABSTRACT

The invention relates to a compound of the formula (VII)

(VII)

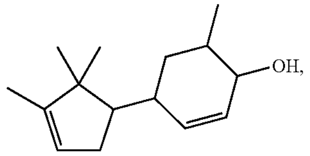

to an odoriferous substance or aroma composition comprising such a compound, and to a perfumed or aromatized product comprising such a compound. The invention furthermore relates to the use of a compound of the formula (VII) as an odoriferous substance and/or for improving fixation of an odoriferous substance or aroma composition. The invention moreover relates to a method for producing a compound of the formula (VII), to a method for producing a precursor of the compound of the formula (VII) and to the precursor itself. It moreover relates to a method for producing, enhancing or modifying a sandalwood odor in a mixture.

14 Claims, No Drawings

6-METHYL-4-(2',2',3'-TRIMETHYL-3'-CYCLOPENTEN-1'-YL)-2-CYCLOHEXEN-1-OL AS SANDAL ODORIFEROUS SUBSTANCE

CROSS-REFERENCE TO RELATED APPLICATION

This application claims benefit of priority in part to European patent application serial no. 07 116 875.1, filed on Sep. 20, 2007, which is incorporated herein by reference in its entirety.

The invention relates to a compound of the formula (VII)

(VII)

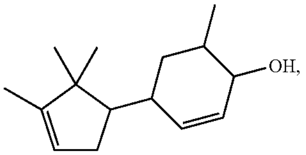

to an odoriferous substance or aroma composition comprising such a compound, and to a perfumed or aromatized product comprising such a compound. The invention furthermore relates to the use of a compound of the formula (VII) as an odoriferous substance and/or for improving fixation of an odoriferous substance or aroma composition. The invention moreover relates to a method for producing a compound of the formula (VII), to a method for producing a precursor of the compound of the formula (VII) and to the precursor itself. It moreover relates to a method for producing, enhancing or modifying a sandalwood odor in a mixture.

PRIOR ART

There is sustained interest in the odoriferous substance industry in the development of new odoriferous substances in order to enable the creation of new perfume oils, for both alcoholic and functional perfumery. Compounds with a woody odor are indispensable components in the fragrance industry. One particularly valuable class of these woody odoriferous substances are compounds with a sandalwood odor. Compounds with a sandalwood odor are frequently structurally characterized by a 4-(2,2,3-trimethyl-cyclopent-3-enyl)-butan-1-ol parent structure, it being possible for the butan-1-ol side chain to be saturated or monounsaturated and mono- or polymethyl-substituted. Some representatives of this class of odoriferous substances are 2-methyl-4-(2',2',3'-trimethyl-3'-cyclopenten-1'-yl)-butan-1-ol (I) (Brahmanol®, Symrise GmbH & Co. KG), 2-ethyl-4-(2',2',3'-trimethyl-3'-cyclopenten-1'-yl)-2-buten-1-ol (II) (Sandranol®, Symrise GmbH & Co. KG), 3-methyl-5-(2',2',3'-trimethyl-3'-cyclopenten-1'-yl)-4-penten-2-ol (III) (Ebanol®, Givaudan S.A.) and 3,3-dimethyl-5-(2',2',3'-trimethyl-3'-cyclopenten-1'-yl)-4-penten-2-ol (IV) (Polysantol®, Firmenich S.A.).

(I)

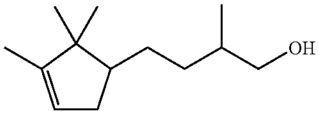

-continued (II)

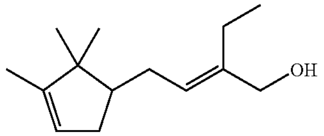

(III)

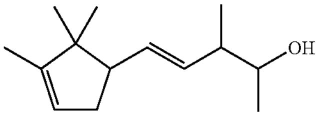

(IV)

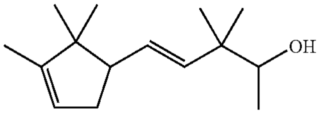

These compounds (I) to (IV) are distinguished by a strong sandalwood odor which varies among the compounds (a) in strength and (b) in further odor aspects of the individual compounds (I)-(IV).

U.S. Pat. No. 5,189,013 discloses compounds which fall within the general formula (V), i.e. compounds, in which a saturated or unsaturated cyclohexanone or cyclohexanol ring is present instead of an alkanol or alkenoyl side chain (as in compounds (I) to (IV)).

(V)

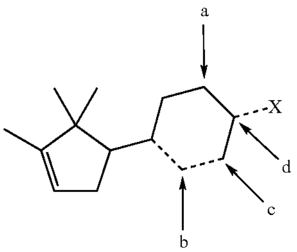

In the formula (V), the exocyclic dashed line means a single bond (in which case X is OH) or a double bond (in which case X is O). According to the general formula (V), the six-membered ring may have one or more methyl substituents in positions a, b, c and d. The disclosed compounds, however, only contain substitutions in positions c and d. Derivatives substituted in position a or b are not listed.

The compounds disclosed in U.S. Pat. No. 5,189,013 in the main exhibit an at most weak sandalwood odor. Only with regard to one compound, namely 1,2-dimethyl-4-(2',2',3'-trimethyl-3'-cyclopenten-1'-yl)-2-cyclohexen-1-ol, is it stated that said compound has an odor whose character is similar to that of natural sandalwood. The stated compound is a compound of the formula (V), with X equal to OH and in which the six-membered ring has a double bond in position 2, i.e. between arrows c and b (corresponds to compound (VIIIa), cf. Table 1). U.S. Pat. No. 5,189,013 furthermore discloses that none of the disclosed compounds which are structurally similar to the latter-stated compound has odor properties which are superior to those of known compounds.

The publications Huaxue Shiji 2000, 22(2), 100-102 and Jingxi Huagong 1999, 16 (Zengkan, Proceedings for '99 China's Symposium on Technology Development and Application of Perfume and Essence), 294-297 describe a mixture (VI), obtained by reduction of 4-(2',2',3'-trimethyl-3'-cyclopenten-1'-yl)-2-cyclohexen-1-one, of 4-(2',2',3'-trimethyl-3'-cyclopenten-1'-yl)-2-cyclohexen-1-ol (VIa, unsaturated cyclohexanol ring, dashed line corresponds to double bond) and 4-(2',2',3'-trimethyl-3'-cyclopenten-1'-yl)-cyclohexan-1-ol (VIb, saturated cyclohexanol ring, dashed line corresponds to single bond), which mixture exhibits a valuable, sandalwood-like aroma.

(VI)

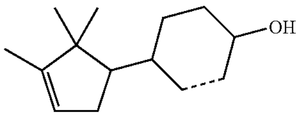

The object of the present invention was to provide a new sandalwood odoriferous substance which has a low odorous threshold value and, with regard to some or all of its secondary properties, is superior to the sandalwood odoriferous substances known from the prior art. Desired secondary properties in this connection were in particular elevated (inherent) tenacity, elevated impact, elevated substantivity, the property of acting as a fixative and the ability to bring about a good blooming effect.

According to the invention, this object is achieved by a compound of the formula (VII).

(VII)

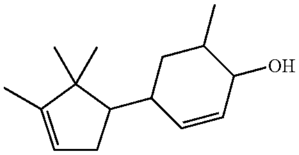

The compound according to the invention (VII) may here preferably be present in the form (a) of a pure optically active enantiomer, (b) of a racemic mixture of the enantiomers of one, two, three, four, five, six, seven or all diastereomeric enantiomeric pairs, or (c) of an optically active mixture of various enantiomers.

The compound of the formula (VII) has four chiral centers, such that there are eight diastereomeric enantiomeric pairs. These eight diastereomeric enantiomeric pairs comprise the following compounds:

(1'R,1R,4R,6R)-6-methyl-4-(2',2',3'-trimethyl-3'-cyclopenten-1'-yl)-2-cyclohexen-1-ol
(1'S,1S,4S,6S)-6-methyl-4-(2',2',3'-trimethyl-3'-cyclopenten-1'-yl)-2-cyclohexen-1-ol
(1'R,1S,4R,6R)-6-methyl-4-(2',2',3'-trimethyl-3'-cyclopenten-1'-yl)-2-cyclohexen-1-ol
(1'S,1R,4S,6S)-6-methyl-4-(2',2',3'-trimethyl-3'-cyclopenten-1'-yl)-2-cyclohexen-1-ol
(1'R,1R,4S,6R)-6-methyl-4-(2',2',3'-trimethyl-3'-cyclopenten-1'-yl)-2-cyclohexen-1-ol
(1'S,1S,4R,6S)-6-methyl-4-(2',2',3'-trimethyl-3'-cyclopenten-1'-yl)-2-cyclohexen-1-ol
(1'R,1R,4R,6S)-6-methyl-4-(2',2',3'-trimethyl-3'-cyclopenten-1'-yl)-2-cyclohexen-1-ol
(1'S,1S,4S,6R)-6-methyl-4-(2',2',3'-trimethyl-3'-cyclopenten-1'-yl)-2-cyclohexen-1-ol
(1'R,1S,4S,6R)-6-methyl-4-(2',2',3'-trimethyl-3'-cyclopenten-1'-yl)-2-cyclohexen-1-ol
(1'S,1R,4R,6S)-6-methyl-4-(2',2',3'-trimethyl-3'-cyclopenten-1'-yl)-2-cyclohexen-1-ol
(1'R,1S,4R,6S)-6-methyl-4-(2',2',3'-trimethyl-3'-cyclopenten-1'-yl)-2-cyclohexen-1-ol
(1'S,1R,4S,6R)-6-methyl-4-(2',2',3'-trimethyl-3'-cyclopenten-1'-yl)-2-cyclohexen-1-ol
(1'R,1R,4S,6S)-6-methyl-4-(2',2',3'-trimethyl-3'-cyclopenten-1'-yl)-2-cyclohexen-1-ol
(1'S,1S,4R,6R)-6-methyl-4-(2',2',3'-trimethyl-3'-cyclopenten-1'-yl)-2-cyclohexen-1-ol
(1'R,1S,4S,6S)-6-methyl-4-(2',2',3'-trimethyl-3'-cyclopenten-1'-yl)-2-cyclohexen-1-ol
(1'S,1R,4R,6R)-6-methyl-4-(2',2',3'-trimethyl-3'-cyclopenten-1'-yl)-2-cyclohexen-1-ol.

Mixtures which are particularly valuable in odor terms are mixtures of the diastereomers of the compound according to the invention, the composition of which yields values on analysis by gas chromatography which correspond to the mass fractions stated in Table 1 or yields values which lie between the relative minimum and maximum mass fractions stated in each case (GC column: Zebron ZB-1 ms F&F 20 m L×0.18 mm ID×0.18 μm df, packing material: 100% dimethylpolysiloxane, manufacturer: Phenomenex, program: 60-12-300° C.); the values stated are the relative mass fractions of the peaks, relative to the (smallest) peak with the retention index 1632, ranked by retention index (cf. Example 1):

TABLE 1

| Retention index | Relative mass fraction |
|---|---|
| 1628 | 1.3-2.0 |
| 1632 | 1.0 |
| 1638 | 3.5-10.0 |
| 1644 | 2.8-8.0 |
| 1651 | 1.0-2.0 |

The compound according to the invention of the formula (VII) has a sandalwood odor which of perfumistic interest and is moreover distinguished by desired secondary properties: in particular, it has elevated (inherent) tenacity, a low odorous threshold value, elevated impact (odor intensity), elevated substantivity, very good fixative properties and a marked blooming effect. This is surprising, in particular against the background of the statements regarding structurally similar compounds made in U.S. Pat. No. 5,189,013 (cf. above).

(Inherent) tenacity, also known as absorptive capacity, describes a compound's ability to adhere to a substrate. Substantivity describes the ability to be absorbed from a usually aqueous phase onto a substrate or also to remain on a substrate after a washing or rinsing operation. This effect is in particular manifested on substrates such as skin, hair and textile fibers (for example cotton, wool, linen, synthetic fibers). The property of being able to act as a "fixative" (fixative properties) means that the corresponding compound brings about tenacity of other odoriferous substances. This may proceed, for example, by a reduction in vapor pressure or odorous enhancement (for example by reducing the threshold value). The blooming effect is the odor perceived over a surfactant-containing aqueous solution.

The compound according to the invention of the formula (VII) exhibits in both the initial odor and the subsequent odor a strong, radiant, attractive, natural sandalwood note with somewhat sweetish milky and musk-like aspects. It is in particular distinguished by its complex sandalwood odor picture which virtually replicates the multifaceted odor of naturally occurring sandalwood oil. The compound according to the invention accordingly has an organoleptically highly valuable intense, natural sandalwood note combined with a surprisingly elevated tenacity. In perfume oil compositions (cf. example 2), it exhibits a positive action over the entire fragrance chord by distinctly enhancing the sandal nature of the composition and offering good tenacity.

In this respect, the compound according to the invention of the formula (VII) surprisingly differs distinctly from the compounds (VIa) and (VIb) described in Huaxue Shiji 2000, 22(2), 100-102 or Jingxi Huagong 1999, 16, 294-297 (cf. Table 2). Compound (VIa) is an sandal odoriferous substance which has a very clean, but consequently substantially "thinner" effect which is not as natural as the compound according to the invention of the formula (VII). Pure compound (VIb) does not even exhibit a sandal odor.

The compound according to the invention of the formula (VII) also differs distinctly in terms of both structure and odor from the compounds described in U.S. Pat. No. 5,189,013 (cf. Table 1). For example, compound (VIIIa) contains an additional methyl group and comprises a tertiary alcohol function (in contrast with the secondary hydroxyl group present in formula (VII)), in addition to the double bond which occurs at a different position in the ring. In odor terms, compound (VIIIa) exhibits a woody note in the initial odor, but this tends more towards cedar wood and patchouli and is not typical of sandal. The subsequent odor of this compound is distinctly weaker than the initial odor. Compound (IXa) is likewise distinguished by a tertiary alcohol function (in contrast with the secondary alcohol function in compound (VII)). This is a weakly woody-smelling compound with a balsamic, ambergris-like (and not sandal-like) secondary note, the initial odor effect of which is stronger than the subsequent odor, which results in the substance lacking expressiveness. Finally, unlike the compound according to the invention of the formula (VII), compound (Xa) does not exhibit a typical sandal note, but instead, after a weak initial odor, subsequently a sweetish woody, Cananga-like note. This compound is only a very weak odoriferous substance.

TABLE 2

| No. | Structure | Odor description |
|---|---|---|
| VIa | 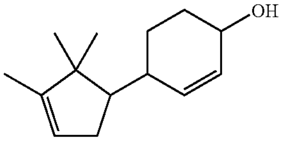 | sandalwood-like note |
| VIb | 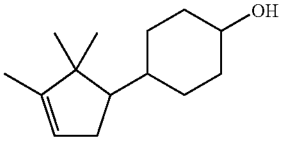 | sweet, musk, animalic |
| VIIIa | 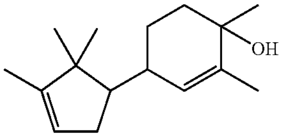 | powerful, woody note with a clear, clean sandalwood nature, which does not develop until the end note* |
| VIIIb | 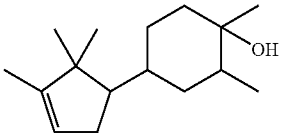 | woody, phenolic, leather, slightly sandalwood* |

TABLE 2-continued

| No. | Structure | Odor description |
|---|---|---|
| VIIIc | 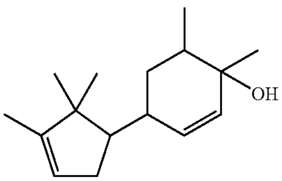 | acetate, wood, very weak sandal note |
| IXa | 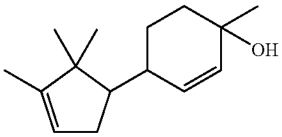 | weakly woody, very slightly sandalwood, fruity* |
| IXb | 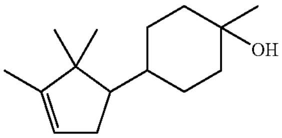 | weak; weak, floral, dirty* |
| Xa | 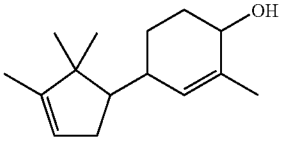 | weak, slightly sandalwood* |
| Xb | 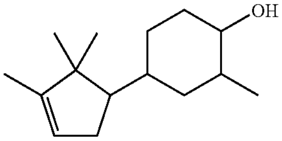 | weak, floral, woody, sandalwood-like* |

*odor descriptions according to U.S. Pat. No. 5,189,013.

It is advantageous to combine the compound according to the invention at least with one further odoriferous substance or an aroma substance and so form a novel odoriferous or aroma substance composition. Interesting and natural novel and original fragrance notes may be created in this manner. Odoriferous substances which are advantageously suitable for combining are listed, for example, in S. Arctander, Perfume and Flavor Materials, vols. I and II, Montclair, N.J. 1969, private publication, or H. Surburg, J. Panten, Common Fragrance and Flavor Materials, 5th edition, Wiley-VCH, Weinheim 2006. Specifically, the following may be mentioned:

extracts of natural raw materials such as essential oils, concretes, absolutes, resins, resinoids, balsams, tinctures such as for example:

ambergris tincture; amyris oil; angelica seed oil; angelica root oil; anise oil; valerian oil; basil oil; tree moss absolute; bay oil; artemisia oil; benzoin resin; bergamot oil; beeswax absolute; birch tar oil; bitter almond oil; savory oil; buchu leaf oil; cabreuva oil; cade oil; calmus oil; camphor oil; cananga oil; cardamom oil; cascarilla oil; cassia oil; cassie absolute; castoreum absolute cedar leaf oil; cedarwood oil; cistus oil; citronella oil; lemon oil; copaiba balsam; copaiba balsam oil; coriander oil; costus root oil; cumin oil; cypress oil; davana oil; dill weed oil; dill seed oil; eau de brouts absolute; oak moss absolute; elemi oil; tarragon oil; eucalyptus citriodora oil; eucalyptus oil; fennel oil; pine-needle oil; galbanum oil; galbanum resin; geranium oil; grapefruit oil; guaiacwood oil;

gurjun balsam; gurjun balsam oil; helichrysum absolute; helichrysum oil; ginger oil; iris root absolute; iris root oil; jasmine absolute; calmus oil; camomile oil, blue; camomile oil, Roman; carrot seed oil; cascarilla oil; pine-needle oil; spearmint oil; caraway oil; labdanum oil; labdanum absolute; labdanum resin; lavandin absolute; lavandin oil; lavender absolute; lavender oil; lemongrass oil; lovage oil; lime oil, distilled; lime oil, pressed; linaloe oil; Litsea cubeba oil; bay leaf oil; mace oil; marjoram oil; mandarin oil; massoia bark oil; mimosa absolute; ambrette oil; musk tincture; muscatel sage oil; nutmeg oil; myrrh absolute; myrrh oil; myrtle oil; clove leaf oil; clove bud oil; neroli oil; olibanum absolute; olibanum oil; opopanax oil; orange blossom absolute; orange oil; origanum oil; palmarosa oil; patchouli oil; perilla oil; Peru balsam oil; parsley leaf oil; parsley seed oil; petitgrain oil; peppermint oil; pepper oil; pimento oil; pine oil; pennyroyal oil; rose absolute; rosewood oil; rose oil; rosemary oil; sage oil, Dalmatian; sage oil, Spanish; sandalwood oil; celery seed oil; spike lavender oil; star anise oil; styrax oil; tagetes oil; fir needle oil; tea tree oil; terpentine oil; thyme oil; Tolu balsam; tonka absolute; tuberose absolute; vanilla extract; violet leaf absolute; verbena oil; vetiver oil; juniper berry oil; Cognac oil; wormwood oil; wintergreen oil; ylang ylang oil; hyssop oil; civet absolute; cinnamon leaf oil; cinnamon bark oil, and fractions thereof, or constituents isolated therefrom;

individual odoriferous substances from the group comprising hydrocarbons, such as for example 3-carene; alpha-pinene; beta-pinene; alpha-terpinene; gamma-terpinene; p-cymol; bisabolene; camphene; caryophyllene; cedrene; famesene; limonene; longifolene; myrcene; ocimene; valencene; (E,Z)-1,3,5-undecatriene; styrene; diphenylmethane;

aliphatic alcohols such as for example hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

aliphatic aldehydes and the acetals thereof such as for example hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethylacetal; 1,1-dimethoxy-2,2,5-trimethyl-4-hexene; citronellyloxyacetaldehyde; 1-(1-methoxypropoxy)-(E/Z)-3-hexene;

aliphatic ketones and the oximes thereof such as for example 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

aliphatic sulfur-containing compounds such as for example 3-methylthio-hexanol; 3-methylthiohexyl acetate; 3-mercaptohexanol; 3-mercaptohexyl acetate; 3-mercaptohexyl butyrate; 3-acetylthiohexyl acetate; 1-menthen-8-thiol;

aliphatic nitriles such as for example 2-nonenoic acid nitrile; 2-undecenoic acid nitrile; 2-tridecenoic acid nitrile; 3,12-tridecadienoic acid nitrile; 3,7-dimethyl-2,6-octadienoic acid nitrile; 3,7-dimethyl-6-octenoic acid nitrile;

esters of aliphatic carboxylic acids such as for example (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl-isobutyrate; hexyl crotonate; ethyl isovalerate; ethyl-2-methyl pentanoate; ethyl hexanoate; allyl hexanoate; ethyl heptanoate; allyl heptanoate; ethyl octanoate; ethyl-(E,Z)-2,4-decadienoate; methyl-2-octinate; methyl-2-noninate; allyl-2-isoamyloxyacetate; methyl-3,7-dimethyl-2,6-octadienoate; 4-methyl-2-pentyl-crotonate;

acyclic terpene alcohols such as for example: citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and the formates, acetates, propionates, isobutyrates, butyrates, isovalerates, pentanoates, hexanoates, crotonates, tiglinates and 3-methyl-2-butenoates thereof;

acyclic terpene aldehydes and ketones such as for example geranial; neral; citronellal; 7-hydroxy-3,7-dimethyloctanal; 7-methoxy-3,7-dimethyloctanal; 2,6,10-trimethyl-9-undecenal; geranyl acetone; and the dimethyl and diethyl acetals of geranial, neral, 7-hydroxy-3,7-dimethyloctanal;

cyclic terpene alcohols such as for example: menthol; isopulegol; alpha-terpineol; terpinenol-4; menthan-8-ol; menthan-1-ol; menthan-7-ol; borneol; isoborneol; linalool oxide; nopol; cedrol; ambrinol; vetiverol; guaiol; and the formates, acetates, propionates, isobutyrates, butyrates, isovalerates, pentanoates, hexanoates, crotonates, tiglinates and 3-methyl-2-butenoates thereof;

cyclic terpene aldehydes and ketones such as for example menthone; isomenthone; 8-mercaptomenthan-3-one; carvone; camphor; fenchone; alpha-ionone; beta-ionone; alpha-n-methyl ionone; beta-n-methyl ionone; alpha-isomethyl ionone; beta-isomethyl ionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4-a-methanonaphthalen-8(5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedarwood oil (methylcedryl ketone);

cyclic alcohols such as for example: 4-tert.-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

cycloaliphatic alcohols such as for example alpha-3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

cyclic and cycloaliphatic ethers such as for example: cineole; cedryl methyl ether; cyclododecyl methyl ether; 1,1-dimethoxycyclododecane; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

cyclic and macrocyclic ketones such as for example 4-tert.-butylcyclohexanone; 2,2,5-trimethyl-5-pentylcyclopentanone; 2-heptylcyclopentanone; 2-pentylcyclo-pentanone; 2-hydroxy-3-methyl-2-cyclopenten-1-one; 3-methyl-cis-2- penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert.-pentylcyclohexanone; 5-cyclohexadecen-1-one; 6,7-dihydro-1,1,2,3,3-pentamethyl-4(5H)-indanone; 8-cyclohexadecen-1-one; 9-cycloheptadecen-1-one; cyclopentadecanone; cyclohexadecanone;

cycloaliphatic aldehydes such as for example 2,4-dimethyl-3-cyclohexene carbaldehyde; 2-methyl-4-(2,2,6-trimethyl-cyclohexen-1-yl)-2-butenal; 4-(4-hydroxy-4-methylpentyl)-3-cyclohexene carbaldehyde; 4-(4-methyl-3-penten-1-yl)-3-cyclohexene carbaldehyde;

cycloaliphatic ketones such as for example 1-(3,3-dimethyl-cyclohexyl)-4-penten-1-one; 2,2-dimethyl-1-(2,4-dimethyl-3-cyclohexene-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl-2,6,10-trimethyl-2,5,9-cyclododecatrienyl ketone; tert.-butyl-(2,4-dimethyl-3-cyclohexen-1-yl) ketone;

esters of cyclic alcohols such as for example 2-tert.-butylcyclohexyl acetate; 4-tert.-butylcyclohexyl acetate; 2-tert.-pentylcyclohexyl acetate; 4-tert.-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5- or 6-indenyl acetate; 4,7-methano-3a,4,5,6,7,7a-hexahydro-5- or 6-indenyl propionate; 4,7-methano-3a,4,5,6,7,7a-hexahydro-5- or 6-indenyl isobutyrate; 4,7-methanooctahydro-5- or 6-indenyl acetate;

esters of cycloaliphatic alcohols such as for example 1-cyclohexylethyl crotonate;

esters of cycloaliphatic carboxylic acids such as for example allyl-3-cyclohexyl propionate; allylcyclohexyl oxyacetate; cis- and trans-methyl dihydrojasmonate; cis- and trans-methyl jasmonate; methyl-2-hexyl-3-oxocyclopentane carboxylate; ethyl-2-ethyl-6,6-dimethyl-2-cyclohexene carboxylate; ethyl-2,3,6,6-tetramethyl-2-cyclohexene carboxylate; ethyl-2-methyl-1,3-dioxolane 2-acetate;

araliphatic alcohols such as for example benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

esters of araliphatic alcohols and aliphatic carboxylic acids such as for example benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenyl-ethyl butyrate; cinnamyl acetate; 2-phenoxyethyl isobutyrate; 4-methoxybenzyl acetate;

araliphatic ethers such as for example: 2-phenyl ethyl methyl ether; 2-phenyl ethyl isoamyl ether; 2-phenyl ethyl 1-ethoxyethyl ether; phenylacetaldehyde dimethylacetal; phenylacetaldehyde diethylacetal; hydratropaldehyde dimethylacetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

aromatic and araliphatic aldehydes such as for example: benzaldehyde; phenylacetaldehyde; 3-phenylpropanal; hydratropaldehyde; 4-methylbenz-aldehyde; 4-methylphenylacetaldehyde; 3-(4-ethylphenyl)-2,2-dimethylpropanal; 2-methyl-3-(4-isopropylphenyl)propanal; 2-methyl-3-(4-tert.-butylphenyl)propanal; 2-methyl-3-(4-isobutylphenyl) propanal; 3-(4-tert.-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

aromatic and araliphatic ketones such as for example: acetophenone; 4-methyl-acetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)ethanone; 2-benzofuranylethanone; (3-methyl-2-benzofuranyl)ethanone; benzophenone; 1,1,2,3,3,6-hexamethyl-5-indanyl methyl ketone; 6-tert.-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

aromatic and araliphatic carboxylic acids and the esters thereof such as for example: benzoic acid; phenylacetic acid; methyl benzoate; ethyl benzoate; hexyl benzoate; benzyl benzoate; methylphenyl acetate; ethylphenyl acetate; geranylphenyl acetate; phenylethylphenyl acetate; methyl cinnamate; ethyl cinnamate; benzyl cinnamate; phenylethyl cinnamate; cinnamyl cinnamate; allyl phenoxy acetate; methyl salicylate; isoamyl salicylate; hexyl salicylate; cyclohexyl salicylate; cis-3-hexenyl salicylate; benzyl salicylate; phenylethyl salicylate; methyl-2,4-dihydroxy-3,6-dimethylbenzoate; ethyl-3-phenyl glycidate; ethyl-3-methyl-3-phenyl glycidate;

nitrogenous aromatic compounds such as for example: 2,4,6-trinitro-1,3-dimethyl-5-tert.-butylbenzene; 3,5-dinitro-2,6-dimethyl-4-tert.-butyl aceto-phenone; cinnamonitrile; 3-methyl-5-phenyl-2-pentenoic acid nitrile; 3-methyl-5-phenylpentanoic acid nitrile; methyl anthranilate; methyl-N-methyl anthranilate; Schiff bases of methyl anthranilate with 7-hydroxy-3,7-dimethyloctanal, 2-methyl-3-(4-tert.-butylphenyl)propanal or 2,4-dimethyl-3-cyclohexene carbaldehyde 6-isopropyl quinoline; 6-isobutyl quinoline; 6-sec.-butyl quinoline; 2-(3-phenylpropyl)pyridine; indole; skatole; 2-methoxy-3-isopropylpyrazine; 2-isobutyl-3-methoxypyrazine;

phenols, phenyl ethers and phenyl esters such as for example: estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenyl acetate;

heterocyclic compounds such as for example: 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

lactones such as for example: 1,4-octanolide; 3-methyl-1,4-octanolide; 1,4-nonanolide; 1,4-decanolide; 8-decen-1,4-olide; 1,4-undecanolide; 1,4-dodecan-olide; 1,5-decanolide; 1,5-dodecanolide; 4-methyl-1,4-decanolide; 1,15-penta-decanolide; cis- and trans-11-pentadecen-1,15-olide; cis- and trans-12-pentadecen-1,15-olide; 1,16-hexadecanolide;

9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

In odoriferous or aroma substance compositions, the amount used of the compound according to the invention preferably amounts to 0.0001 to 90 wt. %, preferably 0.01 to 70 wt. % and particularly preferably 0.1 to 50 wt. %, relative to the total amount of the odoriferous or aroma substance composition.

Odoriferous or aroma substance compositions which contain the compound according to the invention may be used for perfuming or aromatization in liquid form, undiluted or diluted with a solvent. Solvents suitable to this end are for example ethanol, isopropanol, diethylene glycol monoethyl ether, glycerol, propylene glycol, 1,2-butylene glycol, dipropylene glycol, diethyl phthalate, triethyl citrate, isopropyl myristate, triacetin, vegetable oils etc.

Ingredients with which the compound according to the invention may be combined are for example:

preservatives, abrasives, antiacne agents, agents against skin ageing, antibacterial agents, anticellulitis agents, antidandruff agents, antiinflammatory agents, irritation-preventing agents, irritation-suppressing agents, antimicrobial agents, antioxidants, astringents, antiperspirant agents, antiseptic agents, antistatic agents, binders, buffers, excipients, chelating agents, cell stimulants, cleaning agents, care agents, depilatory products, surface-active substances, deodorizing agents, antiperspirants, plasticizers, emulsifiers, enzymes, essential oils, fibers, film formers, fixatives, foaming agents, foam stabilizers, substances for preventing foaming, foam boosters, fungicides, gelling agent, gel-forming agents, hair care products, hair styling products, hair smoothing products, moisture-donating agents, moisturizing substances, moisture-retaining substances, bleaching agents, starching agents, stain-removing agents, optical brighteners, impregnating agents, soil-repelling agents, friction-reducing agents, slip agents, moisture creams, ointments, opacifiers, plasticizing agents, hiding agents, polishing agents, lustrants, polymers, powders, proteins, moisturizing agents, abrasive agents, silicones, skin-soothing agents, skin-cleaning agents, skin-conditioning agents, skin-healing agents, skin-lightening agents, skin-protecting agents, skin-softening agents, cooling agents, skin-cooling agents, warming agents, skin-warming agents, stabilizers, UV-absorbing agents, UV filters, laundry detergents, rinse conditioners, suspending agents, skin-tanning agents, thickeners, vitamins, oils, waxes, fats, phospholipids, saturated fatty acids, mono- or polyunsaturated fatty acids, $\alpha$-hydroxy acids, polyhydroxyfatty acids, liquefying agents, dyes, color-protective agents, pigments, anticorrosion agents, aromas, flavorings, odoriferous substances, polyols, surfactants, electrolytes, organic solvents or silicone derivatives.

Moreover, odoriferous or aroma substance compositions according to the invention which contain the compound according to the invention may be adsorbed on a carrier which ensures both a fine distribution of the odoriferous or aroma substances in the product and controlled release on use. Such carriers may be porous inorganic materials such as sodium sulfate, silica gels, zeolites, gypsums, clays, clay granules, aerated concrete etc., or organic materials such as woods, cellulose-based substances, sugars, dextrins (for example maltodextrin), or plastics such as PVC, polyvinyl acetates or polyurethanes. The combination of composition according to the invention and carrier is one example of an article according to the invention.

Odoriferous or aroma substance compositions which contain the compound according to the invention may also be microencapsulated, spray-dried, be present as inclusion complexes or as extrusion products (i.e. products according to the invention) and be added in this form for example to a product which is to be perfumed or aromatized.

Optionally, the properties of the compositions modified in this way may be further optimized with regard to more targeted fragrance release by "coating" with suitable materials, for which purpose waxy plastics such as for example polyvinyl alcohol are preferably used. The resultant products are in turn products according to the invention.

The odoriferous or aroma substance compositions according to the invention may be encapsulated to yield products according to the invention, for example, by "coacervation" methods with the assistance of capsule materials for example made from polyurethane-type substances or soft gelatin. Spray-dried odoriferous or aroma substance compositions may be produced for example by spray drying an emulsion or dispersion containing the odoriferous or aroma substance composition, wherein modified starches, proteins, dextrin and vegetable gums may be used as carriers. Inclusion complexes may be produced for example by introducing dispersions of the odoriferous or aroma substance composition and cyclodextrins or urea derivatives into a suitable solvent, for example water. Extrusion products may be produced by melting the odoriferous or aroma substance compositions with a suitable waxy substance and extrusion with subsequent solidification, optionally in a suitable solvent, for example isopropanol.

The compound according to the invention and odoriferous substance compositions which contain the compound according to the invention may be used in concentrated form, in solutions or in an above-described modified form for the production of perfumed products according to the invention such as for example perfume extracts, eaux de parfum, eaux de toilette, shaving lotions, eaux de cologne, pre-shave products, splash colognes, and perfumed tissue wipes and for perfuming acidic, alkaline and neutral cleaning agents, such as for example floor cleaners, window cleaners, dishwashing detergents, bath and sanitary cleaners, scouring cream, solid and liquid toilet cleaners, pulverulent and foam carpet cleaners, textile fresheners, ironing aids, liquid detergents, pulverulent detergents, laundry pretreatment agents, such as bleaches soaking agents and stain removers, laundry rinse conditioners, laundry soaps, laundry tablets, disinfectants, surface disinfectants as well as air fresheners in liquid or gel form or applied to a solid carrier, aerosol sprays, waxes and polishes such as furniture polishes, floor waxes and shoe polishes as well as body care products such as for example solid and liquid soaps, shower gels, shampoos, shaving soaps, shaving foams, bath oils, cosmetic emulsions of the oil-in-water, water-in-oil and water-in-oil-in-water type such as for example skin creams and lotions, face creams and lotions, sunscreen creams and lotions, after-sun creams and lotions, hand creams and lotions, foot creams and lotions, depilatory creams and lotions, after-shave creams and lotions, tanning creams and lotions, hair care products such as for example hair sprays, hair gels, strengthening hair lotions, hair rinses, permanent and semi-permanent hair dyes, hair styling agents such as cold waving and hair straightening agents, hair tonics, hair creams and lotions, deodorants and antiperspirants such as for example underarm sprays, roll-ons, deodorant sticks, deodorant creams, decorative cosmetic products such as for example eyeshadow, nail varnish, make-up products, lipstick, mascara, as well as candles, lamp oils, incense sticks, insecticides, repellents and fuels.

The compound according to the invention may be incorporated into products which are aromatized or to be aromatized, in particular preparations serving for nutrition, oral care or pleasure. Such products regularly comprise constituents which have functions other than aromatization or fragrancing (for example dyes) and/or are an already finished commercial product (for example perfume oil).

Preparations serving for nutrition or pleasure are for example bakery products (for example bread, dry cookies, cakes, other pastry products), confectionery (for example chocolates, chocolate bar products, other bar products, fruit gums, hard and soft caramels, chewing gum), alcoholic or non-alcoholic beverages (for example coffee, tea, wine, beverages containing wine, beer, beverages containing beer, liqueurs, spirits, brandies, fruit-containing carbonated beverages, isotonic beverages, soft drinks, nectars, fruit and vegetable juices, fruit or vegetable juice preparations), instant beverages (for example instant cocoa beverages, instant tea beverages, instant coffee beverages), meat products (for example ham, fresh or cured sausage preparations, spiced or marinated fresh or cured meat products), eggs or egg products (dried egg, egg white, egg yolk), cereal products (for example breakfast cereals, muesli bars, precooked ready rice products), dairy products (for example milk beverages, milk ice cream, yoghurt, kefir, curd cheese, soft cheese, hard cheese, dried milk powder, whey, butter, buttermilk, partially or fully hydrolyzed milk protein-containing products), products made from soy protein or other soybean fractions (for example soy milk and products made therefrom, soy lecithin-containing preparations, fermented products such as tofu or tempe or products made therefrom, soy sauces), fruit preparations (for example jams, fruit ice cream, fruit sauces, fruit fillings), vegetable preparations (for example ketchup, sauces, dried vegetables, deep-frozen vegetables, precooked vegetables, pickled vegetables, preserved vegetables), snack articles (for example baked or fried potato chips or potato dough products, bread dough products, maize- or peanut-based extrudates), fat- or oil-based products or emulsions thereof (for example mayonnaise, remoulade, dressings, seasoning preparations), other ready-to-serve meals and soups (for example dried soups, instant soups, precooked soups), spices, seasoning mixtures and in particular powdered seasonings, which are used for example in snack food applications. Once the compound according to the invention has been incorporated, these preparations are preparations according to the invention (as an example of products according to the invention).

Preparations according to the invention may for example assume the form of a semifinished product or a seasoning mixture.

Preparations according to the invention may in particular serve as a semifinished product for the production of further preparations serving for nutrition or pleasure, in particular in spray-dried form. Preparations according to the invention may also be nutritional supplements in the form of capsules, tablets (uncoated and coated tablets, for example coatings resistant to gastric juices), sugar-coated tablets, granules, pellets, mixtures of solids, dispersions in liquid phases, as emulsions, as powders, as solutions, as pastes or as other swallowable or chewable preparations.

Preparations according to the invention serving for oral care are in particular oral and/or dental care products such as toothpastes, tooth gels, tooth powders, mouthwashes, chewing gum and other oral care products.

Further conventional active ingredients, basic materials, auxiliary substances and additives for preparations according to the invention serving for nutrition, oral care or pleasure may be present in quantities of 5 to 99.999999 wt. %, preferably of 10 to 80 wt. %, relative to the total weight of the preparation. The preparations may furthermore comprise water in an amount of up to 99.999999 wt. %, preferably of 5 to 80 wt. %, relative to the total weight of the preparation.

According to a preferred development, the preparations according to the invention (as examples of products according to the invention) containing the compound according to the invention are produced by incorporating the compound according to the invention as the substance without solvent, as a solution (for example in ethanol, water or 1,2-propylene glycol) or in the form of a mixture with a solid or liquid carrier (for example maltodextrin, starch, silica gel), other aromas or aroma substances, and optionally further auxiliaries and/or stabilizers (for example natural or artificial polysaccharides and/or vegetable gums such as modified starches or gum arabic) into a base preparation serving for nutrition, oral care or pleasure. Advantageously, preparations assuming solution and/or suspension or emulsion form may also be converted by spray drying into a solid preparation according to the invention (semifinished product).

The spray-dried solid preparations according to the invention (as an example of products according to the invention) are particularly suitable as semifinished products for producing further preparations according to the invention. The spray-dried solid preparations according to the invention preferably contain 50 to 95 wt. % carriers, in particular maltodextrin and/or starch, 5 to 40% auxiliary substances, preferably natural or artificial polysaccharides and/or vegetable gums such as modified starches or gum arabic.

According to a further preferred embodiment, preparations according to the invention may be produced by incorporating the compound according to the invention and optionally other constituents of the preparation according to the invention into emulsions, into liposomes, for example starting from phosphatidyl choline, into microspheres, into nanospheres or also into capsules, granules or extrudates prepared from a matrix suitable for foodstuffs and products serving for pleasure, for example prepared from starch, starch derivatives (for example modified starch), cellulose or cellulose derivatives (for example hydroxypropylcellulose), other polysaccharides (for example dextrin, alginate, curdlan, carageenan, chitin, chitosan, pullulan), natural fats, natural waxes (for example beeswax, carnauba wax), or from proteins, for example gelatin or other natural products (for example shellac). In said embodiment, depending on the matrix, the products may be obtained by spray drying, spray granulation, melt granulation, coacervation, coagulation, extrusion, melt extrusion, emulsion methods, coating or other suitable encapsulation methods and optionally a suitable combination of the above-stated methods In a further preferred method for producing a preparation according to the invention, the compound according to the invention is initially complexed with one or more suitable complexing agents, for example with cyclodextrins or cyclodextrin derivatives, preferably $\alpha$- or $\beta$-cyclodextrin, and used in this complexed form.

A particularly preferred preparation according to the invention is one in which the matrix is selected such that the compound according to the invention is released in delayed manner by the matrix, such that a long-lasting effect is obtained. A fat, wax, polysaccharide or protein matrix is particularly preferred in this respect.

Further constituents which may be used for preparations according to the invention serving for nutrition or pleasure are conventional basic and auxiliary substances and additives for foodstuffs or products serving for pleasure, for example water, mixtures of fresh or processed, plant or animal basic or raw materials (for example raw, roasted, dried, fermented, smoked and/or boiled meat, bone, cartilage, fish, vegetables, fruit, herbs, nuts, vegetable or fruit juices or pastes or mixtures thereof), digestible or non-digestible carbohydrates (for example sucrose, maltose, fructose, glucose, dextrins, amylose, amylopectin, insulin, xylans, cellulose, tagatose), sugar alcohols (for example sorbitol, erythritol), natural or hardened fats (for example tallow, lard, palm fat, coconut oil, hardened vegetable fat), oils (for example sunflower oil, peanut oil, maize germ oil, olive oil, fish oil, soy oil, sesame oil), fatty acids or the salts thereof (for example potassium stearate), proteinogenic or non-proteinogenic amino acids and related compounds (for example gamma-aminobutyric acid, taurine), peptides (for example glutathione), native or processed proteins (for example gelatin), enzymes (for example peptidases), nucleic acids, nucleotides, taste-correcting agents for unpleasant taste impressions, further taste modulators for further, generally not unpleasant taste impressions, other taste-modulating substances (for example inositol phosphate, nucleotides such as guanosine monophosphate, adenosine monophosphate or other substances such as sodium glutamate or 2-phenoxypropionic acid), emulsifiers (for example lecithins, diacylglycerols, gum arabic), stabilizers (for example carageenan, alginate), preservatives, (for example benzoic acid, sorbic acid), antioxidants (for example tocopherol, ascorbic acid), chelating agents (for example citric acid), organic or inorganic acidulants (for example malic acid, acetic acid, citric acid, tartaric acid, phosphoric acid), bitter substances (for example quinine, caffeine, limonin, amarogentin, humulone, lupulone, catechins, tannins), mineral salts (for example sodium chloride, potassium chloride, magnesium chloride, sodium phosphate), substances preventing enzymatic browning (for example sulfite, ascorbic acid), essential oils, plant extracts, natural or synthetic dyes or coloring pigments (for example carotenoids, flavonoids, anthocyans, chlorophyll and the derivatives thereof), spices, trigeminally active substances or plant extracts containing such trigeminally active substances, synthetic, natural or nature-identical aroma substances or odoriferous substances and odor-correcting agents.

Dental care preparations (as the base for preparations serving for oral care) which contain the compound according to the invention in general comprise an abrasive system (abrasive or polishing agent), such as for example silicas, calcium carbonates, calcium phosphates, aluminum oxides and/or hydroxyapatites, surface-active substances such as for example sodium lauryl sulfate, sodium lauryl sarcosinate and/or cocamidopropyl betaine, humectants such as for example glycerol and/or sorbitol, thickeners, such as for example carboxymethylcellulose, polyethylene glycols, carrageenan and/or Laponite®, sweeteners, such as for example saccharin, taste-correcting agents for unpleasant taste impressions, taste-correcting agents for further, generally not unpleasant taste impressions, taste-modulating substances (for example inositol phosphate, nucleotides such as guanosine monophosphate, adenosine monophosphate or other substances such as sodium glutamate or 2-phenoxypropionic acid), cooling active ingredients such as for example menthol, menthol derivatives (for example L-menthol, L-menthyl lactate, L-menthyl alkylcarbonates, menthone ketals, menthane carboxamides), 2,2,2-trialkylacetamides (for example 2,2-diisopropylpropionic acid methylamide), icilin and icilin derivatives, stabilizers and active ingredients, such as for example sodium fluoride, sodium monofluorophosphate, tin difluoride, quaternary ammonium fluorides, zinc citrate, zinc sulfate, tin pyrophosphate, tin dichloride, mixtures of different pyrophosphates, triclosan, cetylpyridinium chloride, aluminum lactate, potassium citrate, potassium nitrate, potassium chloride, strontium chloride, hydrogen peroxide, aromas and/or sodium bicarbonate or odor-correcting agents).

Chewing gums (as a further example of preparations serving for oral care) which contain the compound according to the invention, in general comprise a chewing gum base, i.e. a chewable mass which becomes plastic on chewing, sugars of various kinds, sugar substitutes, other sweet-tasting substances, sugar alcohols, taste-correcting agents for unpleasant taste impressions, other taste modulators for further, generally not unpleasant taste impressions, taste-modulating substances (for example inositol phosphate, nucleotides such as guanosine monophosphate, adenosine monophosphate or other substances such as sodium glutamate or 2-phenoxypropionic acid), humectants, thickeners, emulsifiers, aromas and stabilizers or odor-correcting agents.

In addition to the compound to be used according to the invention, the preparations according to the invention may also contain an (additional) aroma composition in order to round off and refine the taste and/or odor of the preparation. Suitable (additional) aroma compositions contain for example synthetic, natural or nature-identical aroma, odoriferous and flavor substances and suitable auxiliary substances and carriers.

It goes without saying that it is preferred, albeit not absolutely essential, for products or odoriferous substance or aroma substance compositions according to the invention to comprise an amount of a compound according to the invention which is olfactorily perceptible as a sandalwood odor note. In this case, the positive primary property of the compound according to the invention (also) clearly takes effect. For some applications, however, it may be advantageous to make use of only the positive secondary properties of the compound according to the invention of the formula (VII).

The present invention also provides a product according to the invention (comprising a compound according to the invention of the formula (VII)), comprising a carrier or a substrate which is in direct contact with the compound according to the invention of the formula (VII) or with the odoriferous substance or aroma composition. Suitable carriers are listed further above.

The present invention also provides the use of a compound according to the invention (a compound of the formula (VII)) as an odoriferous substance.

Due to the use of the compound according to the invention of the formula (VII) it is possible to obtain sandalwood notes, which are very strongly reminiscent of sandalwood oil, in the resultant perfume compositions (odoriferous substance mixtures) even at a low rate of addition, the overall odorous impression being made strikingly harmonious, radiance being perceptibly increased and fixation, i.e. the tenacity of the perfume composition, being distinctly enhanced (cf. Example 2).

In comparison with commercially obtainable sandal odoriferous substances such as Ebanol® (III) or Polysantol® (IV), compound (VII) exhibits a similar threshold value, impact and blooming effect (this is the odor perceived over a surfactant-containing aqueous solution) and a similar intensity. However, compound (VII) is distinguished, in particular in comparison with Polysantol® (IV), by substantially higher (inherent) tenacity. The compound according to the invention of the formula (VII) may therefore in particular be used as a fixative in perfume compositions. The compound according to the invention of the formula (VII) moreover exhibits remarkable substantivity.

On the basis of the desired secondary properties of the compound according to the invention of the formula (VII), the present invention accordingly also provides use of the compound according to the invention for improving the fixation of an odoriferous substance or aroma substance composition, it being preferred also to make simultaneous use of the compound according to the invention as an odoriferous substance.

As is additionally explained in greater detail below (cf. the synthetic pathway according to scheme 1 and Example 1), the compound according to the invention of the formula (VII) may be synthesized particularly economically.

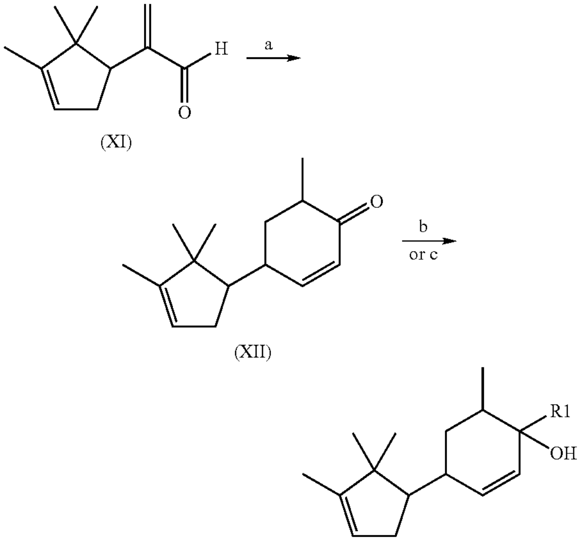

(XI)

(XII)

(VII): R1 = H
(VIIc): R1 = Me a) 2-Methylacetoacetic acid ethyl ester, cat. KOtBu, tBuOH; b) $LiAlH_4$, $Et_2O$; c) MeMgCl, THF.

As is clear from scheme 1, synthesis of the compound according to the invention of the formula (VII) passes via an intermediate, namely a compound of the formula (XII)

(XII)

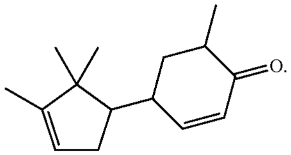

.

This intermediate is novel and thus also provided by the invention.

The present invention accordingly also provides a method for producing a compound of the formula (XII)

(XII)

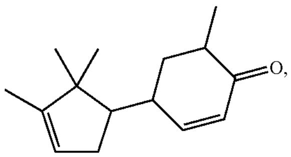

, comprising the steps providing α-methylenecampholenealdehyde of the formula (XI)

(XI)

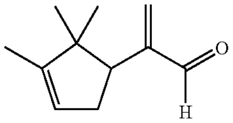

reacting the provided α-methylenecampholenealdehyde of the formula (XI) with 2-methylacetoacetic acid ethyl ester in a base-catalyzed cyclization reaction.

In terms of mechanism, the method according to the invention probably involves a tandem Michael addition/aldol reaction and in situ lactonization and decarboxylation, with 2-methylacetoacetic acid ethyl ester being reacted in the presence of potassium tert.-butanolate as base (cf. J. Org. Chem. 1997, 62, 9323-9325).

The invention also relates to a method for producing the compound according to the invention (VII) with the following steps:

providing or producing a compound of the formula (XII), (XII)

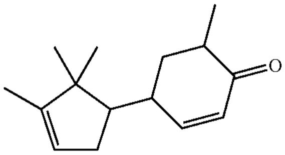

and reducing the compound (XII), such that the compound according to the invention (VII) is formed.

In the method according to the invention for producing the compound of the formula (VII), the compound is preferably reduced with a reducing agent such as lithium aluminum hydride.

Starting from the compound of the formula (XI), the compound of the formula (VII) may be produced in a preferred method according to the invention in a total of two steps. Scheme 1 shown above illustrates the reaction steps to be performed, with R1 being H for the compound of the formula (VII).

The synthetic pathway shown in scheme 1 differs distinctly from the method for producing the comparison substances described in U.S. Pat. No. 5,189,013. The compounds described in U.S. Pat. No. 5,189,013 are synthesized starting from α-campholenealdehyde, which is converted into an enamine and then reacted with alkyl vinyl ketone in a Michael addition. Cyclization then proceeds to yield the corresponding 2-cyclohexenone derivatives by Aldol condensation and further derivatizations to yield the various alcohols.

In contrast, in the production method described in scheme 1, base-catalyzed cyclization of α-methylenecampholenealdehyde (XI) with 2-methylacetoacetic acid ethyl ester proceeds in the first step to yield cyclohexenone derivative (XII). The latter may be converted by further reaction steps known to a person skilled in the art into the compounds of the formulae (VII) (R1=H) and (VIIIc) (R1=Me). Reducing the compound (XII) gives rise to the secondary alcohol (VII) according to the invention, while a Grignard reaction with methylmagnesium chloride yields the tertiary alcohol (VIIIc).

The invention also relates to a method for producing, enhancing or modifying a sandalwood odor in a mixture, comprising the following steps:

providing a compound according to the invention, providing a composition of other constituents and mixing the composition of other constituents with an amount of the compound according to the invention which is sufficient (a) to produce a sandalwood odor in the resultant complete mixture, (b) to enhance an existing sandalwood odor in the composition of other constituents or (c) to modify an existing sandalwood odor in the composition of other constituents.

The following, non-limiting Examples illustrate the invention in further detail.

Data relating to retention indices (RI) in the gas chromatography (GC) of Examples 1.1 and 1.2 relate to the following GC column: Zebron ZB-1ms F&F 20 m L×0.18 mm ID×0.18 μm df, packing material: 100% dimethylpolysiloxane, manufacturer: Phenomenex, program: 60-12-300° C.

EXAMPLE 1

Synthesis of 6-methyl-4-(2',2',3'-trimethyl-3'-cyclopenten-1'-yl)-2-cyclohexen-1-ol (VII)

EXAMPLE 1.1

Synthesis of 6-methyl-4-(2',2',3'-trimethyl-3'-cyclopenten-1'-yl)-2-cyclohexen-1-one (XII)

A solution of 2-methylacetoacetic acid ethyl ester (3.75 g, 26 mmol) and α-methylenecampholenealdehyde (XI) (4.27 g, 26 mmol) in 25 mL of tert.-butanol is combined in portions with potassium tert.-butanolate (1.46 g, 13 mmol) at 15° C. with stirring. The reaction mixture is then heated to reflux for three hours. The reaction solution is worked up by being cooled to room temperature, combined with dilute hydrochloric acid (15 mL) and diluted with diethyl ether. Once the phases have separated, the organic phase is washed to neutrality with dilute sodium hydroxide solution, with saturated sodium chloride solution and with distilled water, dried over sodium sulfate and evaporated under a vacuum. Purification of the crude product by column chromatography on silica gel (mobile solvent: cyclohexane/ethyl acetate 20/1) gives rise to 6-methyl-4-(2',2',3'-trimethyl-3'-cyclopenten-1'-yl)-2-cyclohexen-1-one (XII) in the form of a colorless oil (3.0 g, 53%).

The $^{1}$H-NMR and $^{13}$C-NMR spectra measured on the product correspond to a mixture of the stereoisomers of the compound 6-methyl-4-(2',2',3'-trimethyl-3'-cyclopenten-1'-yl)-2-cyclohexen-1-one (XII).

GC peak 1 (RI=1671):

MS (EI): m/z=41 (37), 53 (21), 55 (33), 67 (68), 77 (26), 79 (36), 81 (48), 91 (29), 93 (35), 95 (84), 109 (100), 110 (35), 147 (43), 203 (27), 218 (15, $M^{\cdot+}$).

GC peak 2 (RI=1676):

MS (EI): m/z=41 (48), 43 (20), 53 (28), 55 (45), 67 (78), 77 (33), 79 (49), 81 (60), 91 (43), 93 (64), 95 (96), 105 (28), 106 (42), 107 (27), 108 (100), 109 (100), 110 (25), 119 (22), 133 (23), 147 (58), 161 (29), 175 (72), 203 (26), 218 (27, $M^{\cdot+}$).

GC peak 3 (RI=1679):

MS (EI): m/z=41 (28), 55 (27), 67 (52), 77 (20), 79 (29), 80 (27), 81 (42), 91 (24), 93 (27), 95 (76), 108 (22), 109 (100), 110 (27), 147 (43), 203 (48), 218 (12, $M^{\cdot+}$).

Odor description of 6-methyl-4-(2',2',3'-trimethyl-3'-cyclopenten-1'-yl)-2-cyclohexen-1-one (XII): woody note tending towards cedar wood.

EXAMPLE 1.2

Synthesis of 6-methyl-4-(2',2',3'-trimethyl-3'-cyclopenten-1'-yl)-2-cyclohexen-1-ol (VII)

6-Methyl-4-(2',2',3'-trimethyl-3'-cyclopenten-1'-yl)-2-cyclohexen-1-one (XII) (1.53 g, 7 mmol), dissolved in 3 mL of diethyl ether, is added dropwise at 15° C. to a suspension of lithium aluminum hydride (133 mg, 3.5 mmol) in 6 mL of diethyl ether. The reaction mixture is stirred for 90 minutes. Working up is performed by hydrolyzing the excess lithium aluminum hydride by addition of a few drops of distilled water and filtering out the resultant precipitate. The organic phase is dried over sodium sulfate and evaporated under a vacuum. Purification of the crude product by column chromatography on silica gel (mobile solvent: cyclohexane/ethyl acetate 3/1) gives rise to 6-methyl-4-(2',2',3'-trimethyl-3'-cyclopenten-1'-yl)-2-cyclohexen-1-ol (VII) in the form of a colorless oil (1.26 g, 81%).

The $^{1}$H-NMR and $^{13}$C-NMR spectra measured on the product correspond to a mixture of the stereoisomers of the compound 6-methyl-4-(2',2',3'-trimethyl-3'-cyclopenten-1'-yl)-2-cyclohexen-1-ol (VII).

GC: RI=1628 (8%), 1632 (5%), 1638 (43%), 1644 (35%), 1651 (8%).

GC peak 1 (RI=1628):

MS (EI): m/z=41 (16), 43 (15), 55 (14), 67 (33), 77 (11), 79 (14), 81 (15), 91 (12), 93 (33), 95 (29), 108 (100), 109 (35), 110 (13), 220 (0.1, $M^{\cdot+}$).

GC peak 2 (RI=1632):

MS (EI): m/z=41 (16), 43 (13), 55 (13), 67 (27), 77 (11), 79 (13), 81 (13), 91 (13), 93 (32), 95 (18), 108 (100), 109 (29), 220 (0.1, $M^{\cdot+}$).

GC peak 3 (RI=1638):

MS (EI): m/z=41 (25), 43 (27), 53 (11), 55 (29), 67 (54), 77 (19), 79 (23), 81 (30), 91 (24), 93 (50), 94 (11), 95 (69), 107 (20), 108 (55), 109 (59), 110 (20), 111 (11), 119 (11), 121 (13), 145 (11), 187 (13), 205 (100), 206 (16), 220 (4, $M^{\cdot+}$).

GC peak 4 (RI=1644):

MS (EI): m/z=29 (10), 41 (29), 43 (34), 53 (12), 55 (33), 67 (70), 77 (21), 79 (26), 81 (35), 91 (25), 93 (46), 94 (13), 95 (84), 96 (13), 105 (11), 107 (18), 108 (71), 109 (100), 110 (53), 111 (15), 119 (12), 121 (14), 145 (11), 159 (12), 187 (17), 220 (7, $M^{\cdot+}$).

GC peak 5 (RI=1651):

MS (EI): m/z=29 (11), 39 (11), 41 (35), 43 (35), 53 (14), 55 (34), 67 (77), 69 (11), 77 (24), 79 (28), 81 (37), 91 (27), 93 (46), 94 (13), 95 (84), 96 (11), 105 (11), 107 (19), 108 (88), 109 (100), 110 (58), 111 (17), 119 (11), 121 (12), 187 (11), 205 (36), 220 (2, $M^{\cdot+}$).

Odor description of 6-methyl-4-(2',2',3'-trimethyl-3'-cyclopenten-1'-yl)-2-cyclohexen-1-ol (VII): strong, radiant, attractive natural sandalwood note with sweetish milky and musk-like aspects

EXAMPLE 2

Perfume Oil Composition

The perfume oil stated below may be used for perfuming various cosmetic products.

Composition:

| Ingredients | Parts by weight |
|---|---|
| Linalyl acetate | 40.0 |
| Oxania type base, 10% in DPG | 1.0 |
| Lilial ®[1] (2-methyl-3-(4-tert-butylphenyl)propanal) | 5.0 |
| Helional ®[2] (alpha-methyl-1,3-benzodioxole-5-propanal) | 2.0 |
| Florosa ®[1] (4-methyl-2-(2-methylpropyl)tetrahydro-2H-4-pyranol) | 5.5 |
| Hydroxycitronellal | 17.0 |
| Mayol ®[3] (cis-4-(1-methylethyl)cyclohexanemethanol) | 5.5 |
| Linalool | 20.0 |
| Citronellol, 10% in DPG | 3.0 |
| Geraniol, 10% in DPG | 2.0 |
| Geranyl acetate, 10% in DPG | 1.0 |
| Neryl acetate, 10% in DPG | 1.0 |
| Benzyl acetate | 7.5 |
| Hedione ®[3] (methyl dihydrojasmonate) | 84.0 |
| Hexylcinnamaldehyde alpha | 6.5 |
| Iraldein gamma | 11.0 |
| Irone alpha, 10% in DPG | 1.0 |
| Vanillin | 7.0 |
| Agrumex HC ®[4], 10% in DPG (2-tert.-butylcyclohexyl acetate) | 1.0 |
| Herbaflorat ®[4], 10% in DPG (4,7-methano-3a,4,5,6,7,7a-hexahydro-5-indenyl acetate and/or 4,7-methano-3a,4,5,6,7,7a-hexahydro-6-indenyl acetate) | 0.5 |
| Cedar wood oil | 3.0 |
| Cashmeran ®[2] (1,2,3,5,6,7-hexahydro-1,1,2,3,3-pentamethyl-4H-inden-4-one) | 5.5 |
| Iso E Super ®[2] (2-acetyl-1,2,3,4,5,6,7,8-octahydro-2,3,8,8-tetramethylnaphthalene) | 290.0 |
| Ambroxide cryst. ®[4] (dodecahydro-3a,6,6,9a-tetramethylnaphtho(2,1-b)furan) | 3.0 |
| Ambrettolide ®[4] (oxacycloheptadec-10-en-2-one) | 7.0 |
| Ethylene brassylate | 70.0 |
| Exaltenone ®[3] ((Z)-4-cyclopentadecen-1-one) | 24.0 |
| Globalide ®®[4] (oxacyclohexadec-12-en-2-one) | 110.0 |
| Helvetolide ®[3] (2-[1-(3,3-dimethylcyclohexyl)ethoxy]-2-methyl-1-propanol propanoate | 2.0 |
| Dipropylene glycol | 143.0 |
| BHT Jonol | 1.0 |
| Total | 880.0 |

DPG = dipropylene glycol
[1]trade name, Givaudan AG, Switzerland;
[2]trade name, International Flavors & Fragrances Inc., USA;
[3]trade name, Firmenich S.A., Switzerland;
[4]trade name, Symrise GmbH & Co. KG, Germany.

The addition of 20 parts by weight of 6-methyl-4-(2',2',3'-trimethyl-3'-cyclopenten-1'-yl)-2-cyclohexen-1-ol (VII) from Example 1.2 results in a distinctly perceptible harmonization of the entire fragrance chord. Furthermore, the intense, natural sandalwood note imparts excellent radiance and complexity to the present composition together with increased tenacity. 6-Methyl-4-(2',2',3'-trimethyl-3'-cyclopenten-1'-yl)-2-cyclohexen-1-ol (VII) here positively asserts its worth.

EXAMPLE 3

Shampoo

6-Methyl-4-(2',2',3'-trimethyl-3'-cyclopenten-1'-yl)-2-cyclohexen-1-ol (VII) (the compound according to the invention) from Example 1.2 was prepared as a 50 wt. % solution in diethyl phthalate and the solution was incorporated at a rate of addition of 0.2 wt. % into a shampoo base of the following formulation (values in wt. %):

| | |
|---|---|
| Sodium lauryl ether sulfate (for example Texapon NSO from Cognis Germany GmbH) | 12% |
| Cocamidopropyl betaine (for example Dehyton K from Cognis Germany GmbH) | 2% |
| Sodium chloride | 1.4% |
| Citric acid | 1.3% |
| Phenoxyethanol, methyl-, ethyl-, butyl-, and propylparaben | 0.5% |
| Peach odoriferous substance mixture comprising gamma-undecalactone | 0.5% |
| Water | 82.3% |

The pH value of the shampoo base was approx. 6. 100 mL of a 20 wt. % aqueous shampoo solution were produced therefrom. Two small strands of hair were washed together in this shampoo solution for 2 minutes and then rinsed for 20 seconds under running, hand-warm water. One strand was wrapped, while wet, in aluminum foil and the second strand was dried with a hairdryer. Both strands of hair were assessed with regard to odor by a panel of odor experts. Both strands of hair exhibited a distinct sandalwood-like odor, the overall impression being judged radiant, rounded, natural and harmonious.

EXAMPLE 4

Rinse Conditioner

The perfume oil composition from Example 2 (after addition of the compound according to the invention (VII) from Example 1.2) was incorporated at a rate of addition 0.5 wt. % in a rinse conditioner base of the following composition (values in wt. %):

| | |
|---|---|
| Quaternary ammonium methosulfate (ester quat), approx. 90% (for example Rewoquat WE 18 from Witco Surfactants GmbH) | 5.5% |
| Alkyl dimethylbenzyl ammonium chloride, approx. 50% (for example Preventol R50 from Bayer AG) | 0.2% |
| Colorant solution, approx. 1% | 0.3% |
| Water | 94.0% |

The pH value of the rinse conditioner base was in the range 2-3. Two pieces of fabric were rinsed in a Linetest machine in the rinse conditioning program for 30 minutes at 20° C. with 370 g of a 1% aqueous rinse conditioner solution. The pieces of fabric were wrung out and then spun for 20 seconds. One piece of fabric was heat-sealed while wet and one was hung up to dry. The two pieces of fabric were then assessed with regard to odor by a panel. Both pieces of fabric exhibited a distinct sandalwood-like odor, the overall impression being judged radiant, rounded, natural and harmonious.

EXAMPLE 5

Washing Powder

The perfume oil composition from Example 2 (after addition of the compound according to the invention (VII) from Example 1.2) was incorporated at a rate of addition of 0.3 wt. % into a washing powder base of the following formulation (all values in wt. %):

| | |
|---|---|
| Linear sodium alkyl benzene sulfonate | 8.8% |
| Ethoxylated fatty alcohol C12-18 (7 EO) | 4.7% |
| Sodium soap | 3.2% |
| Defoamer | |
| DOW CORNING(R) 2-4248S | |
| POWDERED ANTIFOAM, | |
| Silicone oil on zeolite as carrier material | 3.9% |
| Zeolite 4A | 28.3% |
| Sodium carbonate | 11.6% |
| Na salt of a copolymer of acrylic and maleic acid (Sokalan CP5) | 2.4% |
| Na silicate | 3.0% |
| Carboxymethylcellulose | 1.2% |
| Dequest 2066 ([[(Phosphonomethyl)imino]bis[(ethylenenitrilo)bis (methylene)]]tetrakis-phosphonic acid, sodium salt) | 2.8% |
| Optical brightener | 0.2% |
| Sodium sulfate | 6.5% |
| Protease | 0.4% |
| Sodium perborate tetrahydrate | 21.7% |
| Odoriferous substance composition with rose odor | 0.3% |
| TAED | 1.0% |

Two pieces of fabric were washed in a Linetest machine in the main washing cycle for 45 minutes at 60° C. with 370 g of a 1% aqueous washing powder liquor (the pH value of the washing powder liquor is distinctly in the basic range). The pieces of fabric were first rinsed for 5 minutes with cold water, wrung out and then spun for 20 seconds. One piece of fabric was heat-sealed while wet and one was hung up to dry. The two pieces of fabric were then assessed by a panel with regard to odor. Both pieces of fabric exhibited a distinct sandalwood-like odor, the overall impression being judged radiant, rounded, natural and harmonious.

EXAMPLE 6

Deodorant Stick

The perfume oil composition from Example 2 (after addition of the compound according to the invention (VII) from Example 1.2) was incorporated at a rate of addition of 0.25 wt. % into a deodorant stick base of the following formulation:

| | wt. % |
|---|---|
| Sodium stearate | 8.0 |
| 1,2-Propylene glycol | 45.0 |
| 4-Methyl-4-phenyl-2-pentanol | 0.3 |
| 2-Hexyldecanoic acid | 0.5 |
| Polyethylene glycol (25) cetearyl ether | 3.0 |
| Ethanol | 20.0 |
| Water | ad 100.0 |

The odor of the deodorant stick itself and the odor perceptible in the vicinity of the armpit after application of the deodorant stick exhibited a distinct sandalwood-like aspect, the overall impression being judged radiant, rounded, natural and harmonious.

EXAMPLE 7

Larger Scale Synthesis of 6-methyl-4-(2',2',3'-trimethyl-3'-cyclopenten-1'-yl)-2-cyclohexen-1-ol (VII)

EXAMPLE 7.1

Larger Scale Synthesis of 6-methyl-4-(2',2',3'-trimethyl-3'-cyclopenten-1'-yl)-2-cyclohexen-1-one (XII)

To a solution of 2-methyl acetoacetate (482 g, 3.34 mol) and α-methylene campholenic aldehyde (XI) (565 g, 3.03 mol) in 1.5 L tert-butanol was added potassium tert-butanolate (17 g, 0.15 mol) at 9° C. The mixture was stirred for 30 min, then a second portion of potassium tert-butanolate (68 g, 0.61 mol) was added. The reaction mixture was heated to reflux for 15 h. After neutralization with hydrochloric acid (2 M) the mixture was diluted with diethyl ether. The organic layer was separated, washed with brine and dist. water, dried (sodium sulfate), and the solvent was removed at reduced pressure to give 866 g of the crude product. The same procedure was performed with a second batch of the same size. The two batches were unified and purified by distillation to give 686 g (52%) of a colourless oil comprising 71% of 6-methyl-4-(2',2',3'-trimethyl-3'-cyclopenten-1'-yl)-2-cyclohexen-1-one (XII) and 17% of its double-bond isomer 6-methyl-4-(2',2',3'-trimethyl-3'-cyclopenten-1'-yl)-3-cyclohexen-1-one (A).

(A)

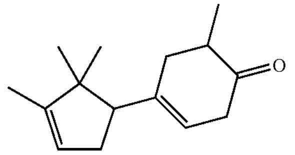

The structure of (A) was confirmed by mass spectrometric and NMR spectroscopic analysis.

Odor description of (A): very weak; technical, green, fruity, woody.

EXAMPLE 7.2

Larger Scale Synthesis of 6-methyl-4-(2',2',3'-trimethyl-3'-cyclopenten-1'-yl)-2-cyclohexen-1-ol (VII)

To a suspension of lithium aluminium hydride (21 g, 0.55 mol) in 1 L diethyl ether was added at 15° C. a portion of the oil obtained in example 7.1 (240 g, 1.11 mol), dissolved in 0.5 L diethyl ether. The reaction mixture was stirred overnight at room temperature and then quenched with dist. water. The precipitate was filtered off and washed with diethyl ether. The mother liquor was dried (sodium sulfate), and the solvent was removed at reduced pressure to give 235 g of the crude product. The same procedure was performed with a second batch of the same size. The two batches were unified and purified by distillation to give 370 g (76%) of a colourless oil comprising 78% of 6-methyl-4-(2',2',3'-trimethyl-3'-cyclopenten-1'-yl)-2-cyclohexen-1-ol (VII) and 21% of double-bond isomer 6-methyl-4-(2',2',3'-trimethyl-3'-cyclopenten-1'-yl)-3-cyclohexen-1-ol (B).

(B)

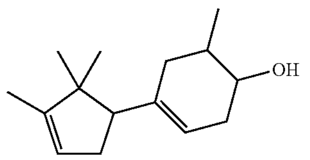

The structure of (B) was confirmed by mass spectrometric and NMR spectroscopic analysis. Diastereomers (B1) and (B2) were isolated by flash chromatography, (B1) containing the cis-1-hydroxy-6-methyl stereoisomers of (B) and (B2) containing the trans-1-hydroxy-6-methyl stereoisomers of (B).

Odor description of (B1): woody, sandalwood, fatty—less valuable than the odor of (VII)

Odor description of (B2): green, fruity, acidic.

The presence of (B) in example 7.2 did not significantly alter the odor character of product (VII).

SPECIFIC EMBODIMENTS

Specific embodiment one comprises a compound of the formula (VII).

(VII)

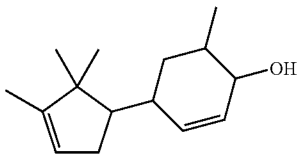

Specific embodiment two comprises the compound as in specific embodiment one, wherein the compound is present in the form (a) of a pure optically active enantiomer, (b) of a racemic mixture of the enantiomers of one, two, three, four, five, six, seven or all diastereomeric enantiomeric pairs, or (c) of an optically active mixture of various enantiomers.

Specific embodiment three comprises an odoriferous substance or aroma substance composition comprising a compound as disclosed in specific embodiment one or specific embodiment two and at least one further odoriferous substance or aroma substance and preferably one or further conventional constituents.

Specific embodiment four comprises a perfumed or aromatized product comprising a compound as in specific embodiment one or two or an odoriferous substance or aroma substance composition as in specific embodiment three.

Specific embodiment five comprises the product as in specific embodiment four, selected from the group consisting of perfume oils and preparations serving for nutrition, oral care or pleasure.

Specific embodiment six comprises the odoriferous substance or aroma substance composition as in specific embodiment three or the product as in specific embodiment four or five, comprising an amount of a compound as in specific embodiment one or specific embodiment two which is olfactorily perceptible as a sandalwood odor note.

Specific embodiment seven comprises the product as in any one of specific embodiments four to six, comprising a carrier or a substrate which is in direct contact with the compound of the formula (VII) or the odoriferous substance or aroma substance composition.

Specific embodiment eight comprises use of a compound as disclosed in specific embodiment one or specific embodiment two as an odoriferous substance.

Specific embodiment nine comprises use of a compound as disclosed in specific embodiment one or specific embodiment two for improving fixation of an odoriferous substance or aroma substance composition.

Specific embodiment ten comprises a compound of the formula (XII).

(XII)

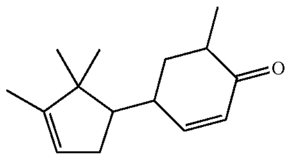

Specific embodiment eleven comprises a method for producing a compound of the formula (XII) as disclosed in specific embodiment ten, comprising the steps:

providing α-methylenecampholenealdehyde of the formula (XI)

(XI)

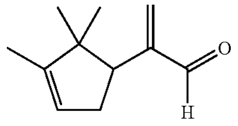

and reacting the provided α-methylenecampholenealdehyde of the formula (XI) with 2-methylacetoacetic acid ethyl ester in a base-catalyzed cyclization reaction.

Specific embodiment twelve comprises a method for producing a compound as disclosed in either of specific embodiment one or specific embodiment two, comprising the steps:

providing or producing a compound of the formula (XII) as disclosed in specific embodiment ten, and reducing the compound of the formula (XII), such that a compound as disclosed in either of specific embodiment one or specific embodiment two is formed.

Specific embodiment thirteen comprises a method for producing, enhancing or modifying a sandalwood odor in a mixture, comprising the following steps:

providing a compound as disclosed in either of specific embodiment one or specific embodiment two, providing a composition of other constituents and mixing the composition of other constituents with an amount of the compound as disclosed in either of specific embodiment one or specific embodiment two, which is sufficient (a) to produce a sandalwood odor in the resultant complete mixture, (b) to enhance an existing sandalwood odor in the composition of other constituents or (c) to modify an existing sandalwood odor in the composition of other constituents.

It is claimed:

1. A compound of the formula (VII), (VII)

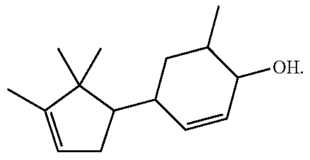

2. The compound as claimed in claim 1, wherein the compound is present in the form (a) of a pure optically active enantiomer, (b) of a racemic mixture of the enantiomers of one, two, three, four, five, six, seven or all diastereomeric enantiomeric pairs, or (c) of an optically active mixture of various enantiomers.

3. An odoriferous substance or aroma substance composition comprising a compound as claimed in claim 1 and at least one further odoriferous substance or aroma substance.

4. A perfumed or aromatized product comprising a compound as claimed in claim 1 or an odoriferous substance or aroma substance composition comprising a compound as claimed in claim 1.

5. The product as claimed in claim 4, selected from the group consisting of perfume oils and preparations serving for nutrition, oral care or pleasure.

6. The odoriferous substance or aroma substance composition as claimed in claim 3, comprising an amount of a compound according to formula VII, which is olfactorily perceptible as a sandalwood odor note.

7. The product as claimed in claim 4, comprising a carrier or a substrate which is in direct contact with the compound of the formula (VII) or the odoriferous substance or aroma substance composition.

8. A method of providing an odoriferous substance comprising applying a compound as claimed in claim 1 to a product.

9. A method of improving fixation of an odoriferous substance or aroma substance composition comprising providing a compound as claimed in claim 1 to a product.

10. A compound of the formula (XII)

(XII)

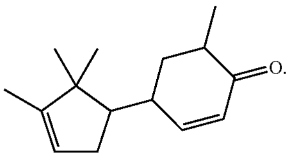

11. A method for producing a compound of the formula (XII) as claimed in claim 10, comprising the steps:

providing α-methylenecampholenealdehyde of the formula (XI)

(XI)

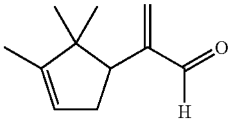

and reacting the provided α-methylenecampholenealdehyde of the formula (XI) with 2-methylacetoacetic acid ethyl ester in a base-catalyzed cyclization reaction.

12. A method for producing a compound as claimed in claim 1, comprising the steps:

providing or producing a compound of the formula (XII), and reducing the compound of the formula (XII), such that a compound as claimed in claim 1 is formed.

13. A method for producing, enhancing or modifying a sandalwood odor in a mixture, comprising the following steps:

providing a compound as claimed in claim 1, providing a composition of other constituents and mixing the composition of other constituents with an amount of the compound as claimed in claim 1, which is sufficient (a) to produce a sandalwood odor in the resultant complete mixture, (b) to enhance an existing sandalwood odor in the composition of other constituents or (c) to modify an existing sandalwood odor in the composition of other constituents.

14. The odoriferous substance or aroma substance of claim 3 further comprising one or more conventional constituents.

* * * * *

UNITED STATES PATENT AND TRADEMARK OFFICE

CERTIFICATE OF CORRECTION

PATENT NO. : 7,569,733 B2 
APPLICATION NO. : 12/209565
DATED : August 4, 2009
INVENTOR(S) : Constanze Brocke et al.

It is certified that error appears in the above-identified patent and that said Letters Patent is hereby corrected as shown below:

-- In Column 7, Line 30, famesene should read: farnesene. --

-- In Column 18, Line 14, please italicize in situ, to read: *in situ.* --

-- In Column 19, Line 21, please underline and insert a colon for the following to read: EXAMPLE 1: --

-- In Column 19, Line 26, please underline and insert a colon for the following to read: EXAMPLE 1.1: --

-- In Column 19, Line 51, please underline the following to read: GC peak 1 (RI=1671): --

-- In Column 19, Line 55, please underline the following to read: GC peak 2 (RI=1676): --

-- In Column 19, Line 61, please underline the following to read: GC peak 3 (RI=1679): --

-- In Column 20, Line 1, please underline and insert a colon for the following to read: EXAMPLE 2.2: --

-- In Column 20, Line 27, please underline the following to read: GC peak 1 (RI=1628) --

-- In Column 20, Line 32, please underline the following to read: GC peak 2 (RI=1632) --

-- In Column 20, Line 37, please underline the following to read: GC peak 3 (RI=1638) --

-- In Column 20, Line 49, please underline the following to read: GC peak 5 (RI=1651): --

-- In Column 20, Line 61, please underline the following to read: EXAMPLE 2 --

UNITED STATES PATENT AND TRADEMARK OFFICE

CERTIFICATE OF CORRECTION

PATENT NO. : 7,569,733 B2
APPLICATION NO. : 12/209565
DATED : August 4, 2009
INVENTOR(S) : Constanze Brocke et al.

It is certified that error appears in the above-identified patent and that said Letters Patent is hereby corrected as shown below:

-- In Column 21, Line 56, please underline the following to read: EXAMPLE 3 --

-- In Column 21, Line 59, please underline the following to read: Shampoo --

-- In Column 21, Line 28, please underline the following to read: EXAMPLE 4 --

-- In Column 21, Line 30, please underline the following to read: Rinse Conditioner --

-- In Column 22, Line 59, please underline the following to read: EXAMPLE 4 --

-- In Column 22, Line 61, please underline the following to read: Washing Powder --

-- In Column 23, Line 45, please underline the following to read: EXAMPLE 6 --

-- In Column 23, Line 47, please underline the following to read: Deodorant Stick --

-- In Column 24, Line 5, please underline the following to read: EXAMPLE 7 --

-- In Column 24, Line 10, please underline the following to read: EXAMPLE 7.1 --

-- In Column 24, Lines 15-19, please italicize tert, to read: *tert* --

-- In Column 24, Line 48, please underline the following to read: EXAMPLE 7.2 --

-- In Column 25, Lines 14-15, italicize cis, to read: *cis*, and trans, to read: *trans* --

UNITED STATES PATENT AND TRADEMARK OFFICE

CERTIFICATE OF CORRECTION

PATENT NO. : 7,569,733 B2 
APPLICATION NO. : 12/209565
DATED : August 4, 2009
INVENTOR(S) : Constanze Brocke et al.

It is certified that error appears in the above-identified patent and that said Letters Patent is hereby corrected as shown below:

-- In Column 25, Line 22, please underline the following to read: SPECIFIC EMBODIMENTS --

Signed and Sealed this

Seventeenth Day of November, 2009

David J. Kappos

David J. Kappos
*Director of the United States Patent and Trademark Office*